US006277407B1

(12) United States Patent
Marius

(10) Patent No.: US 6,277,407 B1
(45) **Date of Patent: *Aug. 21, 2001**

(54) APPARATUS AND METHOD FOR TABLET FABRICATION

(76) Inventor: Frederick S. Marius, 41 Myrtle Ter., Winchester, MA (US) 01890

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/189,280

(22) Filed: Nov. 10, 1998

(51) Int. Cl.[7] ..................... A61K 9/20
(52) U.S. Cl. ..................... 424/464; 424/465
(58) Field of Search ..................... 425/345, 353, 425/231, 227; 264/39, 120; 424/465, 464, 489, 439, 440, 441, 466, 484, 486, 488

(56) References Cited

U.S. PATENT DOCUMENTS

| | | | | |
|---|---|---|---|---|
| 1,345,208 | * | 6/1920 | Majewski | 425/345 |
| 1,692,322 | * | 11/1928 | Aiken | 425/345 |
| 2,851,361 | * | 9/1958 | Diller . | |
| 2,889,226 | * | 6/1959 | Hinkley . | |
| 3,639,169 | | 2/1972 | Broeg et al. | 424/154 |
| 3,653,941 | | 4/1972 | Bell et al. | 117/33.5 |
| 3,660,107 | | 5/1972 | Mayer | 99/66 |
| 3,667,962 | * | 6/1972 | Fritzberg et al. . | |
| 3,692,896 | * | 9/1972 | Tsumura et al. | 424/78 |
| 3,721,725 | * | 3/1973 | Briggs et al. | 264/6 |
| 3,801,251 | * | 4/1974 | Coscia | 425/229 |
| 4,004,036 | | 1/1977 | Schmitt | 426/285 |
| 4,031,238 | | 6/1977 | Reid et al. | 426/285 |
| 4,317,649 | * | 3/1982 | Boellmann | 425/150 |
| 4,384,005 | | 5/1983 | McSweeney | 426/250 |
| 4,459,315 | | 7/1984 | Salo | 426/590 |
| 4,508,740 | | 4/1985 | McSweeney | 426/250 |
| 4,569,650 | * | 2/1986 | Kramer | 425/353 |
| 5,017,122 | | 5/1991 | Staniforth | 425/100 |
| 5,254,355 | | 10/1993 | Smith et al. | 426/285 |
| 5,297,897 | * | 3/1994 | Venrooij et al. | 425/227 |
| 5,417,984 | | 5/1995 | Banker et al. | 424/488 |
| 5,834,472 | * | 11/1998 | Sangekar et al. | 514/252 |
| 5,922,351 | * | 7/1999 | Daher | 424/465 |

FOREIGN PATENT DOCUMENTS

| | | | |
|---|---|---|---|
| 0533021 | * | 3/1993 | (EP) . |
| 10235634 | * | 3/1993 | (JP) . |

OTHER PUBLICATIONS

Murphy and Hollenbeck 'A Unique Application of Extrusion for the Preparation of Water–Soluble Tables,' *Pharmaceutical Technology*, 94–104, (1998)*

* cited by examiner

*Primary Examiner*—James M. Spear
(74) *Attorney, Agent, or Firm*—Sampson & Associates, P.C.

(57) ABSTRACT

A rotary tablet press is provided for the manufacture of water soluble tablets by compression of powdered tablet material which does not include hydrophobic lubricants such as magnesium stearate. The tablet press includes a plurality of dies rotatable around a central axis of the press, and upper and lower punches which are rotatable with the dies and slidably mounted for compressive engagement with the dies. A feeder is provided for introducing the powder tablet material through a feed frame and into the dies. The feed frame includes a cam surface for removing the completed tablets from the dies. A brush is rigidly fastened to the feed frame and adapted to engage the working faces of the upper and lower punches to remove tablet material buildup therefrom after each of the punches has released the tablets. The brush is fabricated from food grade materials and includes bristles which extend obliquely relative to the faces of the upper and lower punches.

27 Claims, 3 Drawing Sheets

APPARATUS AND METHOD FOR TABLET FABRICATION

BACKGROUND OF THE INVENTION

1. Field of the Invention

This invention relates to tablet fabrication, and more particularly to the production of tablets through the use of a tableting press that compresses powders and granules.

2. Background Information

Tableting presses have long been utilized to manufacture tablets by compressing powders and granules. A typical tableting press uses a cylindrical die center made of steel, and steel punches, to compress the powder under relatively high pressures, typically up to about 10 to 15 tons per square inch. One result of the compression is the production of heat. This heat builds up on the face of punches and in the die and, over a relatively short period of time, tends to cause the powder to stick to the faces of the punches and sides of the die. Once the powder begins to stick to the die and/or to the punch faces, the integrity of the tablet is compromised, since as the faces of the punches pull apart to eject the tablet, the tablet sticks to the punch faces and breaks, or is broken or damaged by the friction with the cylindrical walls of the die. Moreover, any powder remaining on the punches and/or die walls tends to add to the volume of powder within the die, to disadvantageously alter the internal pressure of the tablets. Tablets formed under excessive pressure may not dissolve properly, while tablets formed under insufficient pressure tend to break prematurely.

In order to reduce the die and face heat, and reduce the sticking on the face of the punches and the sides of the dies, it has been common practice to add powdered lubricants to the powdered tablet composition. These lubricants generally encase the powdered granules to reduce the friction on the face of the punches and the sides of the die. Commonly used lubricants include magnesium stearate and other stearates, such as sodium stearate and calcium stearate. Stearates tend to be useful as lubricants because of their relatively high viscosity and insolubility in water, which helps prevent their breakdown when used to make compressed tablets.

While the use of stearates may be satisfactory in some applications, such as in the production of pharmaceuticals, their use tends to be undesirable in tablets that are dissolved in water prior to ingestion. Due to their hydrophobic nature, the stearates tend to float to the top of the water when a tablet made using stearates is dissolved in water, creating an undesirable metallic sheen or film on the surface of the water.

Thus, when manufacturing a water soluble tablet it is important to reduce or eliminate any insoluble material in the composition. One attempt to manufacture water soluble tablets involves replacing hydrophobic lubricants, such as stearates, with water soluble lubricants such as polyethylene glycol. While the use of such water soluble lubricants tends to reduce sticking on the sides of the die, these lubricants by themselves do not adequately prevent the tablet composition from sticking to the faces of the punches. This sticking problem is particularly acute when producing relatively large tablets, in which the tablet tends to be pulled apart when the punches separate prior to the tablet's ejection from the press. In particular, over multiple cycles, the composition adhered to the faces of the punches tends to accumulate to undesirable levels to the point at which uniform tablets may no longer be produced.

Thus, a need exists for an apparatus and method for fabricating water soluble tablets which overcomes the drawbacks of the prior art.

SUMMARY OF THE INVENTION

According to an embodiment of this invention, a tablet press is provided for the manufacture of a tablet by compression of tablet material in the form of powder or granules. The tablet press includes at least one die circuitously moveable about the press and adapted for receiving tablet material therein; and a first punch and a second punch, the first and second punches being circuitously moveable with, and being adapted for operative engagement with, the at least one die. A punch movement device is adapted to alternately move at least one of the first and second punches relatively towards and away from an other of the first and second punches to alternately compress the tablet material in the at least one die to form the tablet, and release the tablet. A punch cleaner is disposed in operative engagement with the first and second punches, the punch cleaner being adapted to remove tablet material from the first and second punches after each of the first and second punches has released the tablet.

The present invention provides, in a second aspect, a rotary tablet press for the manufacture of a tablet by compression of tablet material in the form of a powder or granules. The rotary press includes a plurality of dies rotatable around a central axis of the press; a plurality of first and second punches rotatable with the dies; a feeder for introducing tablet material to each of the dies at a filling station; and a punch movement device adapted to alternately move the first and second punches relatively towards and away from one another to alternately compress the tablet material in the dies between working faces of the upper and lower punches to form tablets, and release the tablets. An ejector is provided for removing the released tablets from the plurality of dies; and a punch cleaner is disposed in operative engagement with the plurality of upper and lower punches, the punch cleaner being adapted to remove tablet material buildup from the working faces after each of the upper and lower punches has released the tablets.

The present invention provides, in a third aspect, a method is provided for fabricating a water soluble tablet adapted to dissolve in non-carbonated water. The method includes the steps of:

(a) providing a tablet press including:
- at least one die circuitously moveable about the press and adapted for receiving tablet material therein;
- a first and second punch, the first and second punches being circuitously moveable with, and being adapted for operative engagement with, the at least one die;
- a punch movement device adapted to alternately move at least one of the first and second punches relatively towards and away from an other of the first and second punches to alternately compress the tablet material in the at least one die to form the tablet, and release the tablet;
- a punch cleaner disposed in operative engagement with the first and second punches, the punch cleaner being adapted to remove tablet material from the first and second punches after each of the first and second punches has released the tablet;

(b) introducing tablet material in the form of powder or granules to the at least one die;

(c) moving the at least one of said first and second punches relatively towards the other of said first and second punches to compress the tablet material within the at least one die to form the tablet;

(d) moving the at least one of said first and second punches relatively away from the other of said first and second punches to release the tablet;

(e) engaging the punch cleaner with said first and second punches to remove tablet material therefrom.

The above and other features and advantages of this invention will be more readily apparent from a reading of the following detailed description of various aspects of the invention taken in conjunction with the accompanying drawings.

DETAILED DESCRIPTION OF THE PREFERRED EMBODIMENTS

Figure 1:
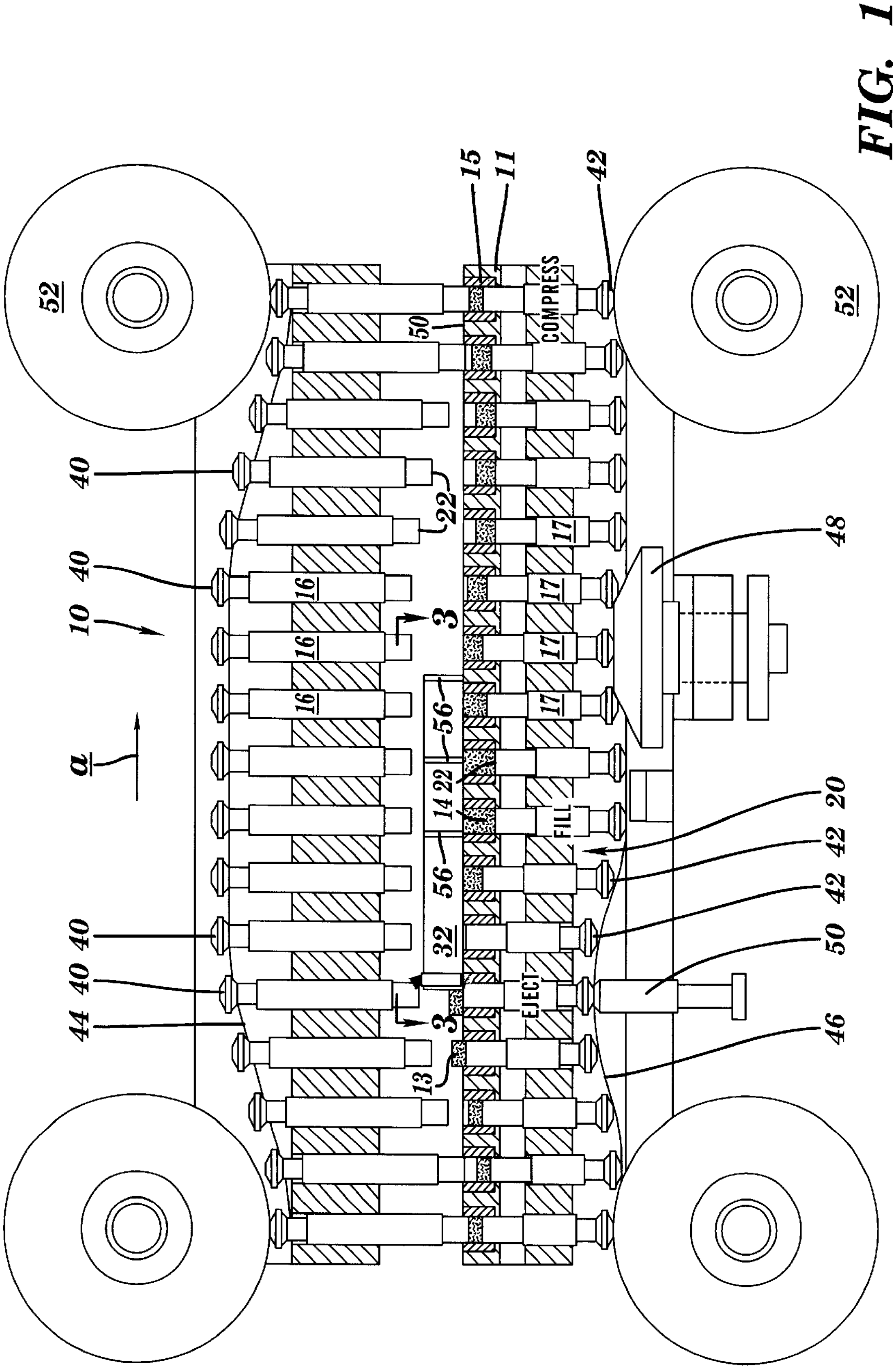
FIG. 1 is a schematic developed plan view, viewed from the interior, of a rotary press incorporating the present invention.
Figure 3:
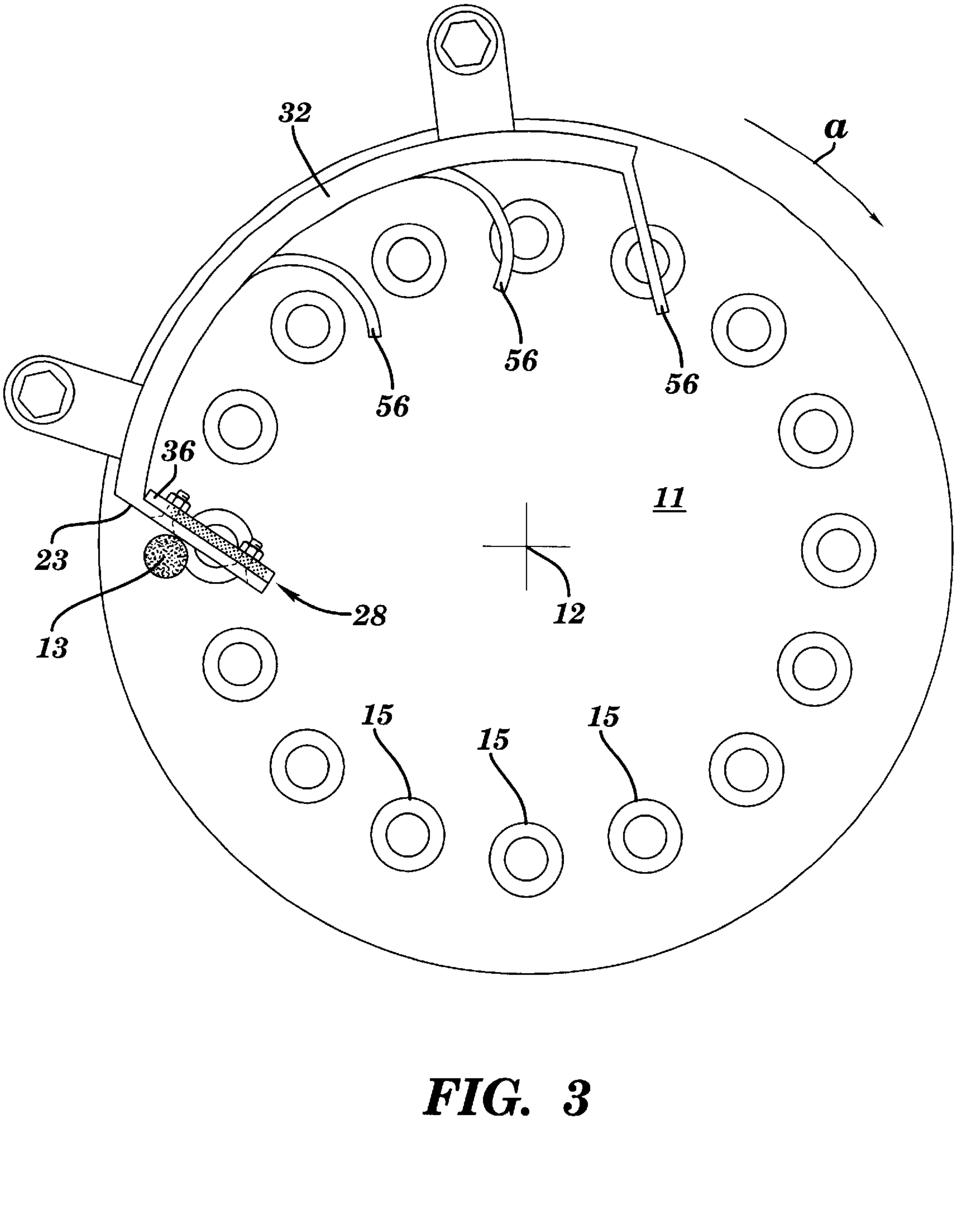
FIG. 3 is a schematic top view of a portion of the press of FIG. 1, taken generally along 3—3 of FIG. 1.

Referring to the figures set forth in the accompanying Drawings, the illustrative embodiments of the present invention will be described in detail hereinbelow. For clarity of exposition, like features shown in the accompanying Drawings shall be indicated with like reference numerals and similar features as shown in alternate embodiments in the Drawings shall be indicated with similar reference numerals.

Where used in this disclosure, the term "axial" shall refer to a direction substantially parallel to rotational axis 12 (FIG. 3). The term "radial" shall refer to a direction substantially orthogonal to the axial direction. The term "coaxial", when used in connection with an element described herein, shall refer to a direction relative to the element, which extends through its geometric center and is substantially parallel to rotational axis 12 of table 11. The terms "downstream" and "upstream" respectively refer to the direction of arrow a (as the dies 15 move through filling station 20) and a direction opposite thereto.

Figure 2:
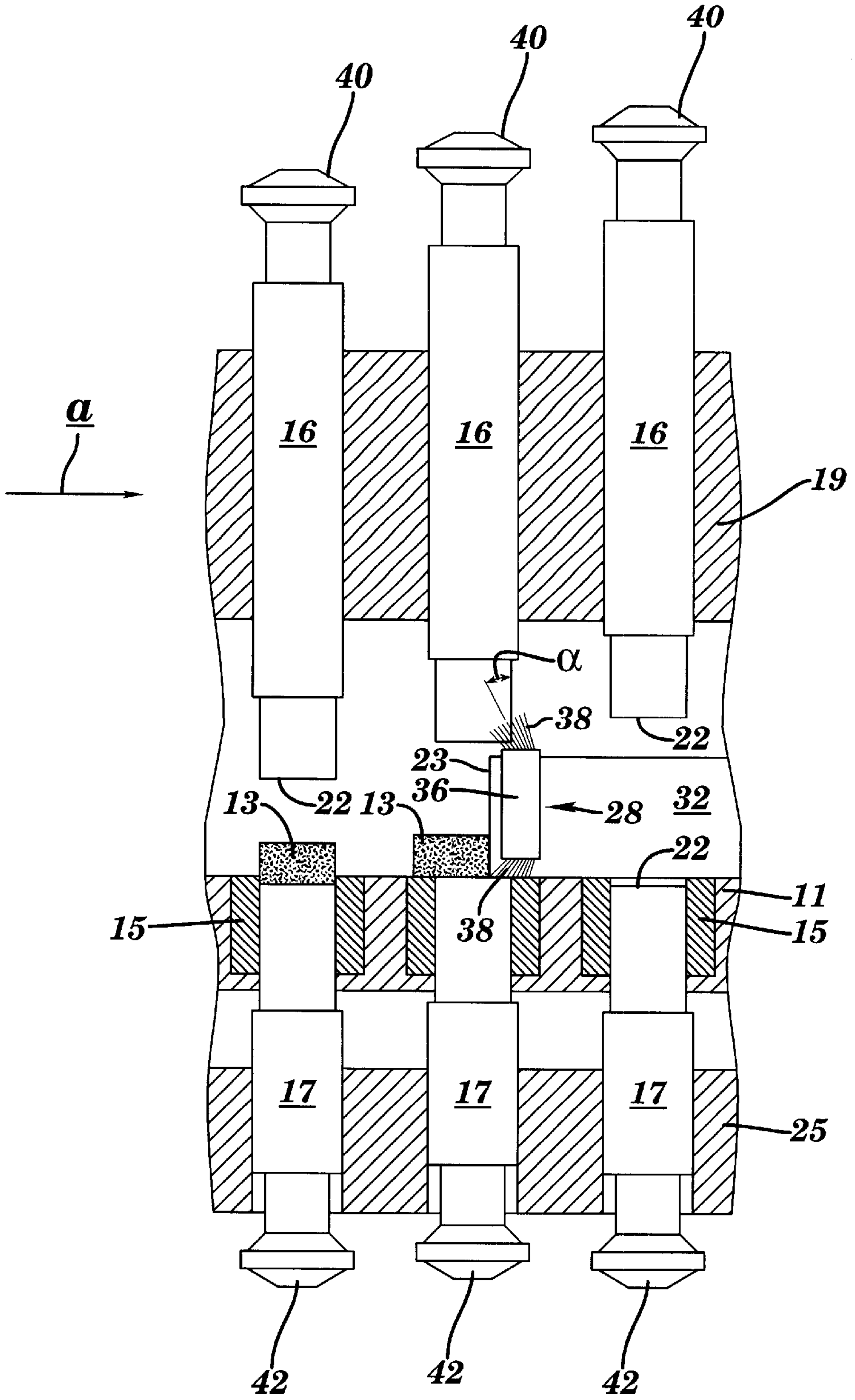
FIG. 2 is an enlarged view of a portion of the rotary press of FIG. 1.

Turning now to the Figures, the rotary press shown in FIGS. 1–3 is in many respects conventional. The press 10 has a circular die table 11 disposed for rotation in direction a about its central axis 12 (FIG. 3). A plurality of generally cylindrical dies 15 are spaced circumferentially within the table 11. Above and coaxially aligned with each die 15 is an associated upper punch 16 mounted for coaxially slidable movement into and away from a die 15 in an upper punch holder 19. The upper punch holder is in turn, arranged for rotation with the die table 11. Each of the upper punches 16 are thus sized for slidable receipt within a corresponding die 15. Similarly, below and coaxially aligned with each die 15 is an associated lower punch 17 disposed for sliding movement into and away from the die 15 in a lower punch holder 25. This lower punch holder is in turn, disposed for rotation with the die table 11 about axis 12. The proximal end of each punch 16 and 17 has a working face 22 which is adapted for engaging and compressing the powder 14 to form tablets 13 as will be discussed hereinbelow. Moreover, each of the upper punches 16 has a cam follower 40 disposed at its distal or upper end, while each of the lower punches 17 has a cam follower 42 at its distal or lower end. The cam followers 40 are supported by and slidably moveable along a stationary upper cam track 44, while the cam followers 42 are similarly supported by, and adapted for slidable movement along stationary lower cam track 46. The die table 11, dies 15, punches 16 and 17 and punch holders 19 and 25 may be fabricated from any suitable material commonly used for fabrication of dies and the like, such as metals and metal alloys, and/or composites, etc.

The lower cam track 46 is interrupted at one position by a ramp 48 the height of which may be screw-adjusted, and at another position by the head of an ejection knob 50 which may also be screw adjustable. A pair of compression rolls 52 are also associated with the upper and lower cam tracks 44 and 46, as will be discussed in greater detail hereinbelow. Since FIG. 1 is a developed view, portions of one end of the drawing, namely compression rolls 52 and one set of punches and a die 15 are duplicated in phantom at the opposite end of the drawing to help illustrate the movement of the punches 16 and 17.

The press 10 includes a hopper (not shown) for feeding powder or granules 14 to be tableted into one or more (two as shown in FIG. 1) dies 15 located at a filling station 20. Powder 14 may include a water soluble lubricant in a preferred embodiment, as will be discussed in greater detail hereinbelow. The hopper feeds the powder into the dies 15 located at the fill station 20 through a feed frame 32 superposed with the top surface 54 of the table 11. The feed frame 32 includes stationary blades 56 which extend radially across the dies for scraping excess powder or granules away from the dies 15 located within the fill station 20 as the dies rotate with table 11 relative to the stationary feed frame 32. This action will be discussed in greater detail hereinbelow with respect to the operation of the present invention.

As best shown in FIGS. 2 and 3, feed frame 32 also includes a tablet cam or ejector 23 which serves to cam the completed tablet 13 radially outward and off of table 11 as the table rotates about its access 12 in direction a. Also disposed on ejector 23 is a brush 28 which includes an elongated base 36 which, as shown in FIG. 3, is adapted to extend transversely or radially across substantially the entire diameter of each die 15 as each die rotates past the ejector 23. As also shown, brush 28 includes a pair of bristle arrays 38 extending from opposite sides of the base or block 36 to respectively engage the faces 22 of punches 16 and 17. As best shown in FIG. 2, the bristle arrays 38 are disposed to resiliently engage and clean the faces 22 of upper and lower punches 16 and 17 as the punches rotate past the brush 28. The bristles within each bristle array 38 are fabricated from any suitable material. In a preferred embodiment the bristles are fabricated from a food grade nylon (polyamide) or polypropylene. Block 36 may be fabricated from any suitable material, such as various metals (i.e steel, stainless steel. etc.) or polymers, (i.e. acetal, nylon, polytetrafluoroethylene, etc.). The bristles are retained within base 36 in any suitable manner familiar to those skilled in the art of brush making. The diameters of the individual bristles as well as the bristle count per cross-sectional unit area are predetermined in conjunction with the elastic modulus of the particular material used, to form bristles which effectively remove any buildup of powder 14 from the punch faces 22, nominally without scoring or otherwise damaging the faces. As also shown in FIG. 2, bristle arrays 38 are preferably angled obliquely towards the incoming punches 16 and 17 (i.e. the bristles extend obliquely towards the upstream direction) to provide a relatively aggressive angle of incidence of the bristles onto faces 22. In a preferred embodiment, bristles are positioned on the block at a 10 degree angle $\alpha$ relative to axis 12, to provide a relatively firm and aggressive contact with the faces 22 of the punches as they rotate through the bristles. In this embodiment, as the faces of the punches rotate through the bristles, the firmness and orientation of the bristles tend to push the punches axially away from the brush, against the bias of the cam tracks 44 and 46 and force any built up powder composition to be removed from the face of the punches 16 and 17. The clean punch faces are then presented to the fill station 20, as will described in greater detail hereinbelow with respect to the operation of the present invention.

Moreover, the bristles are preferably provided with a variable length, so that relatively downstream bristles extend further from surface 50 than relatively upstream bristles as shown in FIGS. 1 and 2. Also as shown, the bristles of array 38 which extends towards lower punches 17 are preferably substantially shorter than those of the bristle array 38 adapted to engage the upper punches 16. This configuration compensates for the relatively small clearance between base 36 of the brush and the surface 50 of table 11. In one example, the bristles have a diameter within a range of from 0.003–0.030 inches (0.007–0.07 cm), with a preferred diameter within a range of approximately 0.0050–0.006 inches (0.012–0.015 cm), with a bristle length within a range of about 0.3–0.5 inches (0.7–1.3 cm) i.e. about 0.5 inches (1.3 cm) on upper array 38, 0.3 inches (0.7 cm ) on lower array 38.

As best shown in FIG. 1, in operation, a given die 15, having an associated upper punch 16 and a lower punch 17, is moved with table 11 to the filling station 20 (i.e. a position axially aligned with feed frame 32) where the die is filled with powder 14. As the die moves to the fill station 20, the cam follower 42 is moved down (axially away) from surface 50 of table 11 by the slope of the cam track 46 so that the lower punch 17 only slightly projects into the die and the die is thus almost entirely filled with powder 14. As table 11 continues to rotate in direction a, the cam follower 42 subsequently reaches the ramp 48 and is driven upwardly (axially towards the surface 50) to expel powder from the die. By the time the cam follower 42 is on top of the ramp 48 (i.e. at the point closest to the working surface 50) the blades 56 will have scraped away any excess powder from the surface of the die which is generally co-planar with surface 50. Thereafter, the lower punch 17 is lowered as the cam follower 42 returns to the cam track 46 and the upper punch 16 drops towards table surface 50 as the cam follower 40 slides down the inclined upper cam track 44. The upper and lower punches 16 and 17 are finally forced together by the compression rollers 52 to compress the powder 14 within the die 15 to form a tablet 13. As table 11 continues to move in direction a, the upper punch 16 is raised until it disengages both the die 15 and the tablet 13. The lower punch 17 is also raised until face 22 thereof is flush with surface 50 of the die table 11, at which stage the tablet is cammed radially outwardly by ejector 23 as best shown in FIGS. 2 and 3. The tablet is then collected by a suitable collection device (not shown). As the tablet 13 is being cammed away from table 11 by ejector 23, the faces 22 of upper and lower punches 16 and 17 are moved into engagement with the bristle arrays 38. This engagement serves to remove a majority of any build up of powder 14 thereon as the punches and die move into the fill station 20 where the cycle of operation is repeated.

Although the present invention is shown and described in conjunction with a single stage rotary press 10, the invention may be incorporated into a conventional multi-stage press in which a plurality of tablets are produced during each revolution thereof. Moreover, the cycle of the press 10 may be modified to include various additional steps such as pre-compression of the powder 14, etc.

The present invention as shown and described herein, may be utilized with powder material 14 either with or without a lubricant. The present invention has been shown to be particularly effective in manufacturing water soluble tablets 13 without the use of conventional hydrophobic lubricants such as magnesium stearate. When fabricating such water soluble tablets 13, the present invention may be utilized either with or without lubricants. In a preferred embodiment however, any suitable water soluble lubricant such as polyethylene glycol (PEG) may be mixed with the powder 14 prior to being fed into dies 15 as discussed hereinabove. Examples of additional water soluble lubricants which may be used in the present invention include crystalline maltitol, sodium benzoate, 1-leucine, starch, and sodium lauryl sulfate.

In a further variation of the subject invention, the powdered or granular material 14 may be pre-ground prior to being fed into the dies 15. For example, the powder 14 may be ground to a predetermined mesh size, preferably to a U.S. standard mesh size within a range of about 10 to 30 to provide a grit size of approximately 0.1356 to 0.0365 inches (3460 to 930 microns). This pre-grind step serves to provide the powder with a substantially homogeneous consistency to advantageously reduce the tendency of the powder to stick to either the dies or faces 22. Such pre-grinding may be utilized with either lubricated or unlubricated powder 14. In a still further embodiment, rather than being substantially cylindrical as shown, the inner surface of the dies 15 may be tapered to have a slightly frusto-conical configuration (not shown) to facilitate removal of the tablets 13 therefrom. In such an embodiment, the inner surface of dies 15 are provided with a predetermined diameter at a point substantially flush with surface 50 of die table 11, with the diameter tapering radially inwardly further from surface 50.

The present invention thus enables the successful production of relatively large production runs (i.e. 200,000 tablets or more) of tablets which are water soluble and thus suitable for non-carbonated soft drinks and sports drinks, etc. Moreover, the invention enables production of relatively large tablets, within a range of about 0.5 to 1.5 inches (1.2 to 3.8 cm) in diameter, having sufficient structural integrity to prevent them from breaking inadvertently during handling, while enabling them to efficiently dissolve in water. In a preferred embodiment, the tablets resist breakage forces within a range of from 8.5 to 14 kilopounds (Kp) using a test well known to those in the tableting industry. Additional steps such as lubricating the tablet material with various water soluble lubricants, pre-grinding the particulate to improve homogeneity, as well as tapering the die walls and lubricating the die walls and/or punch faces may be utilized either individually or in various combinations, with the brush 28 of the present invention to effect consistent and repeatable tableting of water soluble powder material.

Although a unitary punch cleaner or brush 28 has been shown and described to clean the punch faces 22, one skilled in the art should recognize that a punch cleaner may be fabricated from one or a plurality of discrete components, such as resilient wipers, sponges, scrapers, brushes, etc., adapted to clean the first and/or second punch faces, without departing from the spirit and scope of the present invention.

The foregoing description is intended primarily for purposes of illustration. Although the invention has been shown and described with respect to an exemplary embodiment thereof, it should be understood by those skilled in the art that the foregoing and various other changes, omissions, and additions in the form and detail thereof may be made therein without departing from the spirit and scope of the invention.

The following illustrative examples are intended to demonstrate certain aspects of the present invention. It is to be understood that these examples should not be construed as limiting.

EXEMPLIFICATION

Example 1

Water soluble drink mix powder including sucrose, dextrose, malto dextrin, citric acid, gum arabic, flavor, salt, acetic acid, and sodium citrate was mixed in four batches with 1 percent crystalline maltitol, 3 percent crystalline maltitol, 1 percent sodium benzoate and 2 percent sodium benzoate by weight, respectively, and fed into a conventional tablet press similar to tablet press 10 without brush 28. All four powder formulations stuck to the walls of the dies. The compositions were tableted on a stokes model "T" single station press.

Example 2

Control

Powder formulations including the drink mix of Example 1 were prepared in five batches including 5 percent mannitol, 0.5 percent 1-leucine, 1 percent 1-leucine, 2 percent 1-leucine, and 10 percent starch by weight, respectively. All five formulations were fed into a tablet press in the manner described in Example 1 and all five formulations resulted in sticking on the die and/or punch face surfaces.

Example 3

A pre-blend of sodium benzoate, PEG 800 and sugar was milled through a number 1 plate. The pre-blend was added to the base drink mix granulation and fed to the tablet press as described in Example 1. The powder stuck to the die wall and/or punch faces.

Example 4

A tablet powder formulation was provided utilizing the drink powder of Example 1 and PEG 3350 lubricant at 0.5 weight percent. The formulation was fed to a stokes rotary DD-2 press having a brush 28 mounted onto the feed frame. The brush had bristles approximately 0.006 inches in diameter fabricated from food grade nylon. A production run of approximately 50,000 tablets was completed with minimal sticking. The size of the tablets was approximately 1 ⅜ inches by 0.5 inches.

Example 5

Seven tablet compositions are provided using the drink powder of Example 1, and 1 weight percent crystalline maltitol, 3 weight percent crystalline maltitol, 1 weight percent sodium benzoate, 2 weight percent sodium benzoate, 1 weight percent 1-leucine, 2 weight percent 1-leucine and 10 percent starch, respectively. All of these formulations are respectively fed to a rotary tablet press substantially as described Example 4. Production runs of at least 50,000 tablets are successfully completed with minimal sticking.

Example 6

The formulations of the previous Example 5 are preground and screened with a screen having a U.S. mesh size of 20, and then tableted substantially as described in the previous Example 5. Successful production runs of at least 50,000 tablets are completed. Example 7

Control

Tablets were fabricated substantially as described in Example 1 in which the die wall and faces 22 were electroplated with a non-stick coating of beryllium. The coating wore off during the production run and generated unacceptable levels of sticking to the punch faces.

Having thus described the invention, what is claimed is:

1. A water soluble soft drink tablet dissolvable in noncarbonated water, fabricated by the process of:

(a) providing tablet material being free of hydrophobic lubricants;

(b) providing a tablet press including:

at least one die circuitously moveable about the press and adapted for receiving tablet materials therein;

a first punch and a second punch each having a working face free of external lubricants, said first and second punches being circuitously moveable with, and being adapted for operative engagement with, said at least one die;

a punch movement device adapted to alternately move at least one of said first and second punches relatively towards and away from an other of said first and second punches to alternately compress the tablet material in said at least one die to form the tablet, and release the tablet;

a punch cleaner having resilient bristles disposable in operative engagement with each of said working faces of said first and second punches to remove tablet material from said working faces after each of said first and second punches has released said tablet;

(c) introducing the tablet material in the form of powder or granules to the at least one die;

(d) moving the at least one of said first and second punches relatively towards the other of said first and second punches to compress the tablet material within the at least one die to form the tablet;

(e) moving the at least one of said first and second punches relatively away from the other of said first and second punches to release the tablet; and (f) engaging the punch cleaner with each of said working faces to remove tablet material therefrom;

wherein said tablet has a diameter in a range of about 0.5 to 1.5 inches (1.2 to 3.8 cm); and said tablet material has a grit size in a range of about 930 to 3460 microns.

2. The tablet of claim 1, wherein said providing step (b) comprises providing a plurality of dies circuitously moveable about said tablet press.

3. The tablet of claim 1, wherein said providing step (b) comprises providing an ejector for removing the tablets from said at least one die.

4. The tablet of claim 2, wherein said providing step (b) further comprises providing a plurality of said first and second punches circuitously moveable with said plurality of dies.

5. The tablet of claim 1, wherein said providing step (b) further comprises the step of enabling said at least one die and said first and second punches to be rotatable around a central axis of the tablet press.

6. The tablet of claim 3, wherein said providing step (b) comprises enabling the working faces of said first and second punches to each alternately engage and release the tablet material in the die.

7. The tablet of claim 6, wherein said providing step (b) comprises adapting the punch cleaner for sliding engagement with said working faces.

8. The tablet of claim 7, wherein said punch cleaner further comprises a brush having said resilient bristles extending from a base, said bristles being adapted for said sliding engagement.

9. The tablet of claim 8, wherein said bristles are fabricated from polyamide.

10. The tablet of claim 9, wherein said bristles have a diameter within a range of about 0.003 to 0.030 inches (0.007 cm to 0.07 cm).

11. The tablet of claim 10, wherein said bristles have a diameter within a range of about 0.005 inches (0.012 cm) to 0.006 in (0.015 cm).

12. The tablet of claim 8, wherein said bristles extend from said base a length within a range of about 0.3 inch to 0.5 inch (0.7 cm to 1.3 cm).

13. The tablet of claim 8, wherein said ejector comprises a feed frame being adapted for movement relative to said at least one die, said feed frame having a surface adapted to engage and cam said tablets from said at least one die.

14. The tablet of claim 13, comprising the step of disposing said brush on said feed frame, and adapting said working face of said first punch to resiliently engage said brush as said first punch moves with said at least one die.

15. The tablet of claim 14, comprising the step of adapting said working face of said second punch to resiliently engage said brush as said second punch moves with said at least one die.

16. The tablet of claim 15, wherein said brush further comprises a plurality of arrays of bristles disposed thereon, wherein at least one of said plurality of arrays is adapted to engage said first punch and at least an other of said plurality of arrays is adapted to engage said second punch.

17. The tablet of claim 16, comprising the step of extending distal ends of bristles of at least one of said plurality of arrays obliquely relative to the direction of movement of said at least one die.

18. The tablet of claim 17, wherein said bristles of at least one of said plurality of arrays extend obliquely upstream relative to the direction of movement of said at least one die.

19. The tablet of claim 17, comprising the step of extending distal ends of bristles of at least an other of said plurality of arrays obliquely relative to the direction of movement of said at least one die.

20. The tablet of claim 19, wherein said bristles of at least an other of said plurality of arrays extend obliquely upstream relative to the direction of movement of said at least one die.

21. The tablet of claim 1, wherein said providing step (a) comprises providing the tablet material with a water soluble lubricant.

22. The tablet of claim 21 wherein said water soluble lubricant is selected from the group consisting of polyethylene glycol, maltitol, sodium benzoate, 1-leucine and starch.

23. The tablet of claim 1, having a thickness of about 0.5 inches (1.2 cm).

24. The tablet of claim 1, having a resistance to breakage forces within a range of from 8.5 to 14 kilopounds.

25. The tablet of claim 1, wherein said providing step (b) comprises the step of providing the at least one die with an inner die wall of frusto-conical configuration.

26. A water soluble soft drink tablet dissolvable in non-carbonated water, fabricated by the process of:

(a) providing tablet material being free of hydrophobic lubricants and being free of $CO_2$ sources;

(b) providing a tablet press including:

at least one die circuitously moveable about the press and adapted for receiving tablet materials therein;

a first punch and a second punch each having a working face free of external lubricants, said first and second punches being circuitously moveable with, and being adapted for operative engagement with, said at least one die;

a punch movement device adapted to alternately move at least one of said first and second punches relatively towards and away from an other of said first and second punches to alternately compress the tablet material in said at least one die to form the tablet, and release the tablet;

a unitary, stationary punch cleaner having resilient bristles disposable in simultaneous operative engagement with each of said working faces of said first and second punches, said bristles extending obliquely upstream relative to the direction of movement of said die, to remove tablet material from said working faces after each of said first and second punches has released said tablet;

(c) introducing the tablet material in the form of powder or granules to the at least one die;

(d) moving the at least one of said first and second punches relatively towards the other of said first and second punches to compress the tablet material within the at least one die to form the tablet;

(e) moving the at least one of said first and second punches relatively away from the other of said first and second punches to release the tablet; and (f) engaging the punch cleaner with said first and second punches to remove tablet material therefrom;

wherein said tablet has a diameter of at least about 0.5 inches (1.2 cm); and said tablet material has a grit size of at least about 930 microns.

27. A method for fabricating a water soluble soft drink tablet dissolvable in non-carbonated water, said method comprising:

(a) providing tablet material being free of hydrophobic lubricants and being free of $CO_2$ sources;

(b) providing a tablet press including:

at least one die circuitously moveable about the press and adapted for receiving tablet materials therein;

a first punch and a second punch each having a working face free of external lubricants, said first and second punches being circuitously moveable with, and being adapted for operative engagement with, said at least one die;

a punch movement device adapted to alternately move at least one of said first and second punches relatively towards and away from an other of said first and second punches to alternately compress the tablet material in said at least one die to form the tablet, and release the tablet;

a unitary, stationary punch cleaner having resilient bristles disposable in simultaneous operative engagement with each of said working faces of said first and second punches, said bristles extending obliquely upstream relative to the direction of movement of said die, to remove tablet material from said working faces after each of said first and second punches has released said tablet;

(c) introducing the tablet material in the form of powder or granules to the at least one die;

(d) moving the at least one of said first and second punches relatively towards the other of said first and second punches to compress the tablet material within the at least one die to form the tablet;

(e) moving the at least one of said first and second punches relatively away from the other of said first and second punches to release the tablet; and (f) automatically engaging the punch cleaner with said first and second punches to remove tablet material therefrom; and (g) sizing and shaping the die and the first and second punches so that said tablet wherein said tablet has a diameter in a range of about 0.5 to 1.5 inches (1.2 to 3.8 cm); and said tablet material has a grit size in a range of about 930 to 3460 microns.

* * * * *